United States Patent [19]

Andreas et al.

[11] Patent Number: 5,613,974
[45] Date of Patent: Mar. 25, 1997

[54] APPARATUS AND METHOD FOR VASCULAR CLOSURE

[75] Inventors: Bernard H. Andreas, Fremont; T. Daniel Gross, Los Gatos; Tomoaki Hinohara; James W. Vetter, both of Portola Valley, all of Calif.

[73] Assignee: Perclose, Inc., Menlo Park, Calif.

[21] Appl. No.: 252,124

[22] Filed: Jun. 1, 1994

Related U.S. Application Data

[63] Continuation-in-part of Ser. No. 989,611, filed as PCT/US93/11864, Dec. 8, 1993, Pat. No. 5,417,699.

[51] Int. Cl.⁶ .................................................. A61B 17/00
[52] U.S. Cl. ........................... 606/144; 606/139; 112/169
[58] Field of Search ................................... 606/139, 144, 606/145, 147, 148, 150; 604/104, 168; 112/169, 80.03

[56] References Cited

U.S. PATENT DOCUMENTS

| | | |
|---|---|---|
| 312,408 | 2/1885 | Wackerhagen . |
| 659,422 | 10/1900 | Shidler . |
| 2,646,045 | 7/1953 | Priestley . |
| 2,959,172 | 11/1960 | Held . |
| 3,470,875 | 10/1969 | Johnson ................................. 606/145 |
| 3,665,926 | 5/1972 | Flores . |
| 3,939,820 | 2/1976 | Grayzel . |
| 4,161,951 | 7/1979 | Scanlan, Jr. . |
| 4,235,177 | 11/1980 | Arbuckle ................................. 606/144 |
| 4,317,445 | 3/1982 | Robinson . |
| 4,493,323 | 1/1985 | Albright et al. . |
| 4,553,543 | 11/1985 | Amarasinghe . |
| 4,587,969 | 5/1986 | Gillis . |
| 4,629,450 | 12/1986 | Suzuki et al. ........................... 604/104 |
| 4,744,364 | 5/1988 | Kensey . |
| 4,852,568 | 8/1989 | Kensey . |
| 4,890,612 | 1/1990 | Kensey ................................... 606/213 |
| 4,929,246 | 5/1990 | Sinofsky ................................. 606/8 |
| 5,021,059 | 6/1991 | Kensey et al. .......................... 606/213 |
| 5,059,201 | 10/1991 | Asnis ...................................... 606/148 |
| 5,061,274 | 10/1991 | Kensey ................................... 606/213 |
| 5,109,780 | 5/1992 | Slouf et al. ............................. 112/169 |
| 5,160,339 | 11/1992 | Chen et al. .............................. 606/158 |
| 5,171,251 | 12/1992 | Bregen et al. ........................... 606/151 |
| 5,192,302 | 3/1993 | Kensey et al. .......................... 606/213 |
| 5,222,974 | 6/1993 | Kensey et al. .......................... 606/213 |
| 5,304,184 | 4/1994 | Hathaway et al. ...................... 606/144 |
| 5,306,254 | 4/1994 | Nash et al. .............................. 604/168 |
| 5,374,275 | 12/1994 | Bradley et al. ......................... 606/144 |
| 5,387,221 | 2/1995 | Bisgaard ................................. 606/148 |
| 5,411,481 | 5/1995 | Allen et al. ............................. 606/144 |

FOREIGN PATENT DOCUMENTS

| | | |
|---|---|---|
| 0140557 | 8/1985 | European Pat. Off. . |
| 1093329 | 5/1984 | U.S.S.R. . |
| 1174036 | 8/1985 | U.S.S.R. . |
| 9405213 | 3/1994 | WIPO . |

OTHER PUBLICATIONS

Product brochure "The Proven Solution to Endoscopic Suturing," Laurus Medical Corporation, Irvine, California Oct. 1994.

REMA–MEDIZINTECHNIK, Gmbh, "Innovation Through Progress," Jan., 1992, pp. 1–8.

*Primary Examiner*—Michael Powell Buiz
*Assistant Examiner*—Jeffrey A. Schmidt
*Attorney, Agent, or Firm*—Townsend and Townsend and Crew LLP

[57] ABSTRACT

A suture-applying device comprises a guide body having a needle guide at its distal end. Needles are reciprocatably carried on a shaft so that they may be advanced through the needle guide and tissue into the guide body. The suturing device is used by placing the needle guide within a vascular puncture. A contact surface is provided on the guide body, and the needle guide is configured so that the vascular wall surrounding the puncture is fully exposed to the needles passing therethrough. The suturing device may be combined with a predilator to form a system for suturing vascular punctures.

62 Claims, 11 Drawing Sheets

APPARATUS AND METHOD FOR VASCULAR CLOSURE

This application is a continuation-in-part of application Ser. No. 07/989,611, filed Dec. 10, 1992 now U.S. Pat. No. 5,417,699 and of application PCT/US93/11864, with an international filing date of Dec. 8, 1993, which claimed priority and continuation-in-part status from application Ser. No. 07/989,611, now U.S. Pat. No. 5,717,699. Both of these applications are incorporated fully herein by reference.

BACKGROUND OF THE INVENTION

1. Field of the Invention

The present invention relates generally to apparatus and methods for the percutaneous closure of body lumens. More particularly, the present invention relates to apparatus and methods for the percutaneous closure of arterial and venous puncture sites, which are usually accessible only through a tissue tract.

A number of diagnostic and interventional vascular procedures are now performed transluminally, where a catheter is introduced to the vascular system at a convenient access location and guided through the vascular system to a target location using established techniques. Such procedures require vascular access which is usually established using the well known Seldinger technique, as described, for example, in William Grossman's "Cardiac Catheterization and Angiography," 3rd Ed., Lea and Febiger, Philadelphia, 1986, incorporated herein by reference.

When vascular access is no longer required, the introducer sheath must be removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time-consuming, frequently requiring one-half hour or more of compression before hemostasis is assured. This procedure is uncomfortable for the patient and frequently requires administering analgesics to be tolerable. Moreover, the application of excessive pressure can at times totally occlude the underlying blood vessel, resulting in ischemia and/or thrombosis. Following manual compression the patient is required to remain recumbent for at least six and at times as long as eighteen hours under close observation to assure continued hemostasis. During this time renewed bleeding may occur resulting in bleeding through the tract, hematoma and/or pseudoaneurism formation as well as arteriovenous fistula formation. These complications may require blood transfusion and/or surgical intervention. The incidence of these complications increases when the sheath size is increased and when the patient is anticoagulated. It is clear that the standard technique for arterial closure can be risky, and is expensive and onerous to the patient. While the risk of such conditions can be reduced by using highly trained individuals, such use is both expensive and inefficient.

To overcome the problems associated with manual compression, the use of bioabsorbable fasteners to stop bleeding has been proposed by several groups. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel, and locating the fastener too far from that surface can result in failure to provide hemostasis and subsequent hematoma and/or pseudo aneurism formation. Conversely, if the fastener intrudes into the arterial lumen, intravascular clots and/or collagen pieces with thrombus attached can form and embolies downstream causing vascular occlusion. Also, thrombus formation on the surface of a fastener protruding into the lumen can cause a stenosis which can obstruct normal blood flow. Other possible complications include infection as well as adverse reactions to the collagen implant.

A more effective approach for vascular closure has been proposed in co-pending application Ser. Nos. 7/989,611 now U.S. Pat. No. 5,417,699; 08/148,809 now U.S. Pat. No. 5,527,322; and PCT/US93/11864. A suture applying device is introduced through the tissue tract with a distal end of the device located at the vascular punctures. One or more needles in the device are then used to draw suture through the blood vessel wall on opposite sides of the punctures, and the suture is secured directly over the adventitial surface of the blood vessel wall to provide highly reliable closure.

While a significant improvement over the use of manual pressure, clamps, and collagen plugs, certain design criteria have been found to be important to successful suturing to achieve vascular closure. For example, it is important that the needles be properly directed through the blood vessel wall so that the suture is well anchored in tissue to provide for tight closure. It is also important that needle deployment within the suturing device be controlled to prevent accidental deployment before the device has been properly introduced to the puncture site in a blood vessel. Additionally, it is important that the vascular suturing device be introduced only to blood vessels which are in a condition to receive it. In particular, because of the expense of the device and potential trauma to the patient, it is important to ascertain whether or not the suturing device can be fully inserted and deployed prior to the actual introduction.

For these reasons, it would be desirable to provide apparatus, systems, and methods for suturing vascular punctures which meet all or some of the criteria discussed above.

2. Description of the Background Art

Devices capable of delivering pairs of needles to various tissue locations are described in the following patents and patent applications: U.S. Pat. Nos. 4,493,323 and 659,422; European patent application 140 557; and U.S.S.R patent applications 1174-036-A and 1093-329-A. A suturing device that carries a pair of needles having suture therebetween is described in a brochure entitled "Innovation through Progress," REMA-MEDIZINTECHNIK, Gmbh, January, 1992. A suturing device having a partially flared cylindrical core for delivering needles to suture anastomoses is described in U.S. Pat. No. 4,553,543. Other suturing and ligating devices are described in U.S. Pat. Nos. 5,171,251; 5,160,339; 4,317,445; 4,161,951; 3,665,926; 2,959,172; 2,646,045; and 312,408. Devices for sealing percutaneous vascular punctures using various plugs and fastener structures are described in U.S. Pat. Nos. 5,222,974; 5,192,302; 5,061,274; 5,021,059; 4,929,246; 4,890,612; 4,852,568; 4,744,364; 4,587,969; and 3,939,820. Collagen fastener sealing devices are under commercial development by Datascope Corp., Montvale, N.J., and Kensey Nash Corporation, Exton, Pa. Copending application Ser. No. 08/148,809, now U.S. Pat. No. 5,527,322 describes a vascular suturing device having a needle guide with a constant peripheral dimension.

SUMMARY OF THE INVENTION

The present invention provides improved apparatus, systems, and methods for suturing percutaneous luminal puncture sites, particularly vascular puncture sites located at the distal end of a percutaneous tissue tract. The improvements are most applicable to paired-needle suturing systems, such as those described in co-pending Application Ser. Nos. 07/989,611 now U.S. Pat. No. 5,417,699 and PCT/US93/11864. At least some of the improvements, however, will be equally applicable to single-needle suturing systems, such as those described in copending application Ser. No. 08/148,809 now U.S. Pat. No. 5,527,322 as well as other types of suturing devices known and described in the medical and patent literature.

In a first aspect of the present invention, a suturing device comprises a guide body, a needle guide connected to and spaced-apart from a distal end of the guide body, and a tissue-receiving region therebetween. The needle guide includes at least one needle guide channel, usually including at least two guide channels for receiving a pair of reciprocatable needles having a length of suture therebetween. A contact surface is provided at the distal end of the guide body and is oriented at an angle in the range from 30° to 80° relative to a central axis of the guide body. The angle is selected to offset the oblique angle at which the guide body typically approaches a vascular punctures site. The oblique angle is the result of the tissue tract which is formed using the well known Seldinger technique. The contact surface is thus able to lie generally flat over the adventitial surface of the blood vessel wall. In this way, the guide body is better positioned to receive needles passing from the needle guide through the tissue-receiving region and into the guide body.

In the second aspect of the present invention, a suturing device comprises a guide body and needle guide, generally as described above. A pair of needles are mounted on a reciprocatable shaft, and the needles and distal portion of the shaft are preferably mounted in a flexible needle sheath. Prior to use, sharpened proximal ends of the needles are located in the guide channels of the needle guide, and proximal reciprocation of the shaft will draw the needles through the guide, through the tissue-receiving region, and to needle-receiving lumens within the guide body. The needle guide has a non-circular profile within the tissue-receiving region which disposes surrounding tissue to provide an improved target for the needles being advanced from the needle guide. In this way, the likelihood that the needles will pass through and become firmly anchored within the tissue surrounding the puncture is greatly increased. Preferably, the non-circular profile is elliptical and the distal end of the needle guide from which the needles emerge is generally circular. The circular profile helps direct the needles past a major face of the elliptical region of the guide, providing a good tissue target for the needles. The circular end of the needle guide also makes and forms a smooth transition with the flexible needle sheath which is preferably attached to the guide.

In a still further preferred embodiment, the needle guide will have a substantially uniform peripheral distance, i.e., total distance around the periphery of any normal cross-section, over the transition from the circular distal end to the elliptical tissue-receiving region. The uniform peripheral distance allows hemostasis at the vascular puncture and allows the puncture periphery to be shaped without distending the tissue to tear and damage the vessel.

In a third aspect of the present invention, a suturing device comprises a guide body, needle guide, pair of needles, and reciprocatable shaft, generally as described above. The suturing device will further comprise a lock or other structure on the guide body for releasably securing the shaft to prevent relative reciprocation. The lock prevents accidental needle deployment while the suturing device is being introduced within the tissue tract. In a preferred embodiment, the lock comprises at least one slot formed at a proximal end of the guide body, preferably within a proximal handle, and at least one key disposed at the proximal end of the shaft. The key is engaged and disengaged in the slot by rotation of the shaft relative to the guide body.

The present invention still further comprises systems and methods for suturing vascular punctures at the distal end of percutaneous tissue tracts. In addition to a suturing device, which may be any of the devices described above, the system also includes a predilator comprising a body, generally a cylindrical body having dimensions similar to the guide body of the suturing device, and a flexible tube attached to a distal end of the body, where the flexible tube has a diameter similar to that of the flexible needle sheath of the suturing device. A guide wire lumen will be formed continuously from the distal end of the flexible tube to the proximal end of the body, and the predilator will further include at least one blood marker lumen extending from a mark port disposed on the flexible tube just distal of the distal end of the body.

According to the method of the present invention, the predilator is first introduced through the tissue tract and into a blood vessel lumen prior to introducing a suturing device. In particular, the flexible tube of the predilator is introduced fully into the blood vessel lumen so that the distal end of the predilator body lies immediately over the adventitial surface of the blood vessel wall. Proper positioning of the predilator can be determined by observing the appearance of blood through the marker lumen which extends to the proximal end of the predilator body. Successful introduction of the predilator dilates the tissue tract in preparation for the suturing device and is predictive of successful introduction of the suturing device. Thus, after the predilator has been successfully introduced (and removed), the suturing device can be introduced and used to suture the vascular puncture, as will be described in detail hereinafter.

DESCRIPTION OF THE SPECIFIC EMBODIMENT

Figure 1:
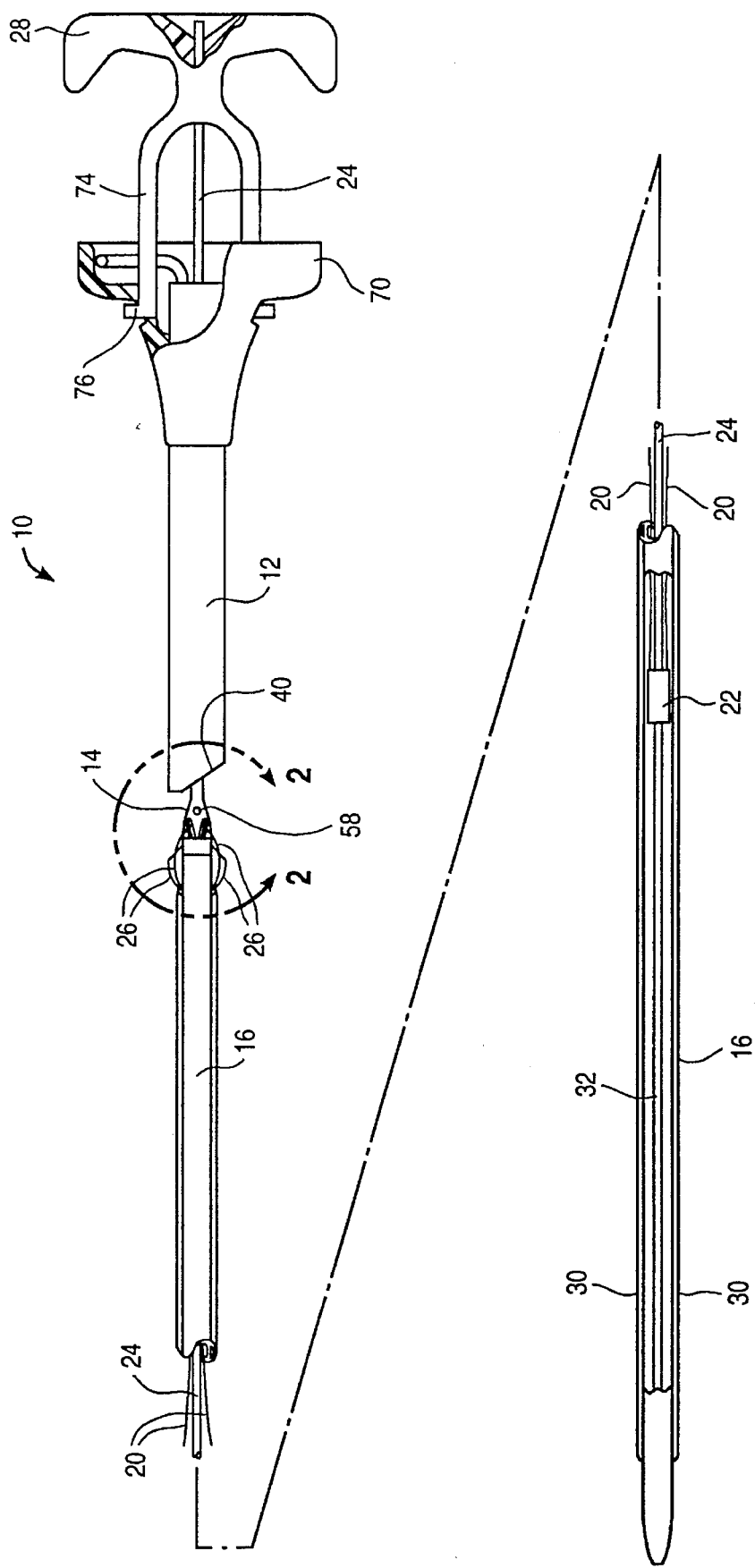
FIG. 1 is a side view of a suturing device constructed in accordance with the principles of the present invention, with portions broken away.

Referring to FIG. 1, a suturing device 10 constructed in accordance with the principles of the present invention comprises a guide body 12, a needle guide 14 secured to a distal end of the guide body 12, and a flexible needle sheath 16 secured to the distal end of the needle guide 14. Four needles 20 (only two of which are shown in FIG. 1 for simplicity) are mounted with their distal ends in a holster 22 attached to a reciprocatable shaft 24. The needles 20 will usually be removably mounted within the holster 22, but optionally could be fixedly attached to the holster, as described in more detail hereinafter. A handle 28 is attached to a proximal end of the shaft 24. The handle 28 can be pulled proximally in order to draw the needles 20 from the sheath 16, through the needle guide 14, and into the guide body 12, as will be described in more detail hereinafter.

The guide body 12 will be sized to be introducible through a percutaneous tissue tract leading to a vascular puncture. In the case of percutaneous punctures made to a patient's femoral artery in the groin, the guide body 12 will typically have a diameter in the range from 5 mm to 12 mm, preferably from 6 mm to 9 mm, and a length generally in a range from 30 mm to 100 mm, preferably from 50 mm to 75 mm. The guide body will define one or more axial lumens therein, typically having a central axial lumen for slidably receiving the shaft 24. One or more additional lumens will usually be provided, preferably four lumens which are radially disposed about the central lumen and which the needles as they are passed from the needle guide 14 into the guide body 12. The guide body 12 will usually be inflexible, preferably being formed at least partially from metal or a hard plastic material. Frequently, the guide body will comprise a metal tubular exterior with a hard plastic insert for defining the desired axial lumen(s).

The flexible needle sheath 16 will be formed from a flexible plastic material, typically from polytetrafluoroethylene (PTFE), fluorinated ethylene propylene (FEP), polyethylene, polyester, polyether block amide, and the like. The sheath 16 will generally be tubular, having a single central lumen, and preferably having at least one side lumens 30 for receiving suture 26 attached to the sharpened proximal ends of needles 20. The side lumen 30 store the suture away from the needles 20 and shaft 24 prior to needle deployment, and the needles 20 draw suture from the side lumens 30 as the needles are advanced proximally. Preferably, a tubular extension 32 is attached to the distal end of holster 22 and acts to provide a continuous and sealed guide wire lumen through the full length of the device 10. The flexible needle sheath 16 will preferably have a diameter in the range from about 2.3 mm (5 F) to 7 mm (21 F), more preferably from 3 mm (9 F) to 4.3 mm (13 F). The length of the sheath 16 will typically be in the range from 200 mm to 400 mm, preferably from 280 mm to 350 mm.

Figure 2:
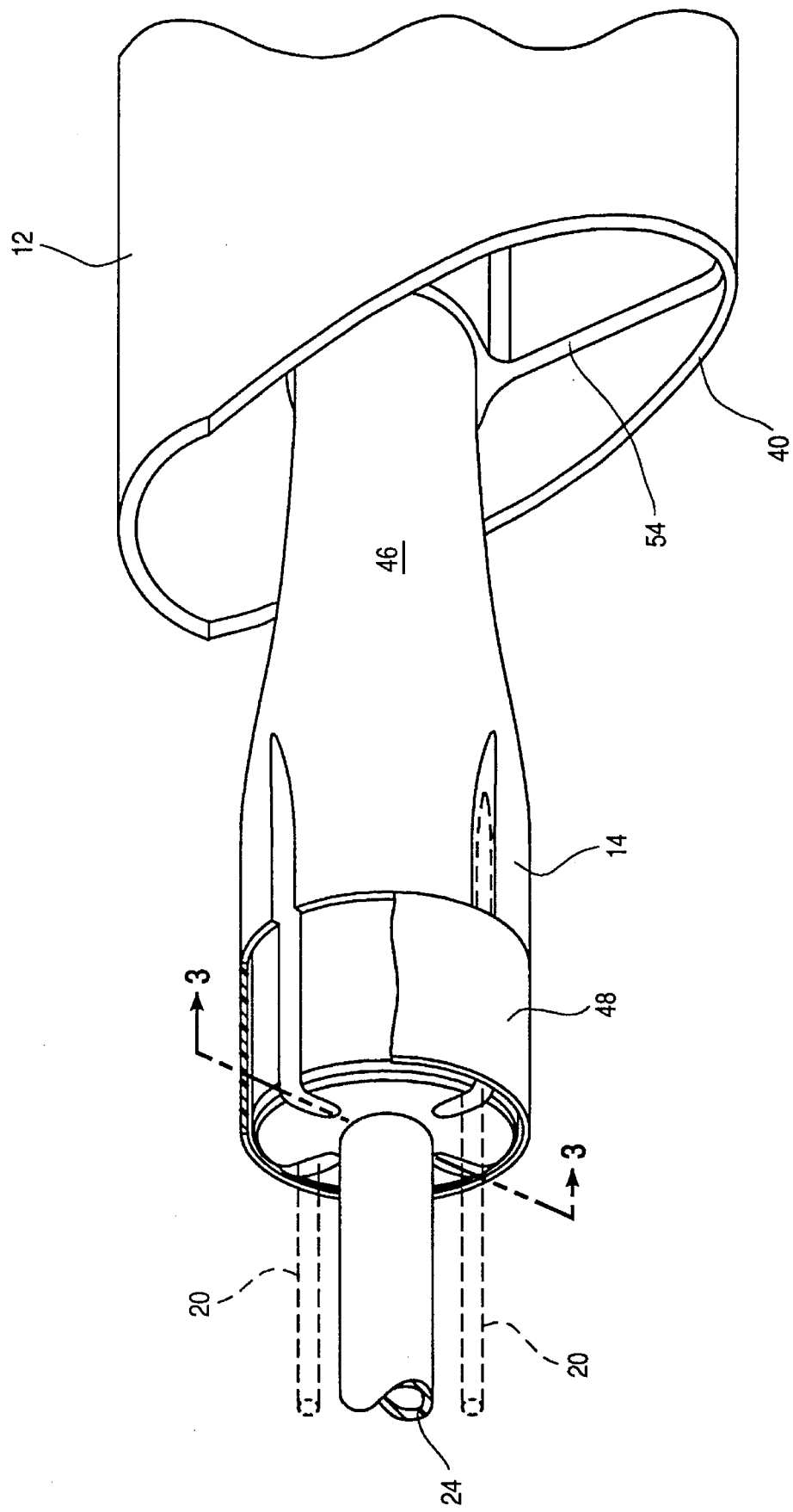
FIG. 2 is a detailed view of the needle guide of the suturing device of FIG. 1, taken along line 2—2 in FIG. 1.

Distal end 40 of the guide body 12 will be configured to provide a contact surface which is oriented at an angle in the range from 30° to 80° preferably from 55° to 70° relative to the central axis of the guide body 12 Most simply, the contact surface will be defined by the distal end of the guide body 12 which has been cut or shaped at the desired angle. In the exemplary embodiment, the surface is defined primarily by the outer peripheral lip of the cylinder which forms the exterior of the guide body 12, as best observed in FIG. 2. The contact surface will span an area in the range from about 40 $mm^2$ to 100 $mm^2$, preferably from 55 $mm^2$ to 75 $mm^2$.

Figure 3:
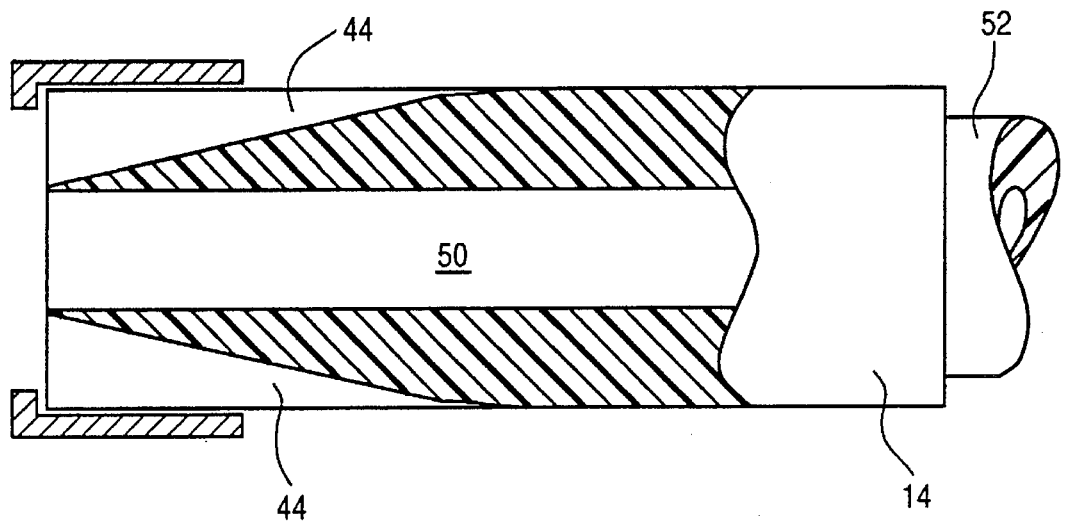
FIG. 3 is an axial, cross-sectional view of the needle guide of FIG. 2, taken along line 3—3 in FIG. 2.

Referring now to FIGS. 2–5, needle guide 14 includes four needle guide channels 44 circumferentially spaced-apart over its distal end. The channels 44 are formed in a radially diverging pattern, as best seen in FIG. 3, so that needles passing through the guide 14 will diverge as they pass through tissue over a tissue-receiving region 46 at the proximal portion of the guide 14. A retaining band 48 is placed over the distal end of the needle guide channels 44 to retain the needles as they pass therethrough. The retaining band 48 may also be used to secure the proximal end of the flexible needle sheath 16. A central lumen 50 is provided axially through the needle guide 14 to allow passage of the shaft 24. An extension 52 of the needle guide 14 is received within a plastic insert 54 inside of the guide body 12. The insert 54 includes a plurality of radially extending partitions which divide the interior of the guide body into needle-receiving lumens, as described in more detail hereinafter. The insert 54 further includes a blood marker lumen (not illustrated) which is connected to a marker port 58 and marker lumen 60 in the needle guide 14.

Figure 4:
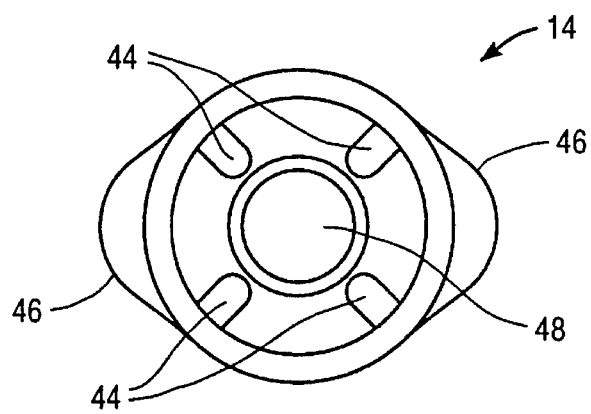
FIG. 4 is a left-end view of the needle guide of FIG. 3.
Figure 5:
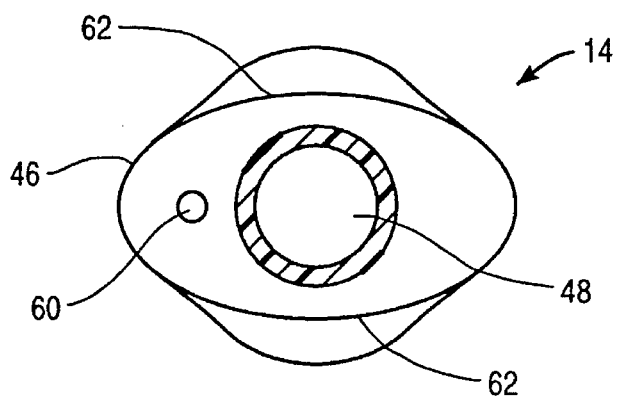
FIG. 5 is a right-end view of the needle guide of FIG. 3.

The needle guide 14 will have a generally circular periphery at its distal end adjacent the retaining band 48. The periphery, however, makes a transition to a generally elliptical tissue-receiving surface 46, as best illustrated in FIGS. 4 and 5. By providing an elliptical profile at the tissue-receiving surface 46, the tissue surrounding the puncture to be closed will be disposed to provide a better target for the needles being passed therethrough. In particular, the needles are oriented to pass over the major surfaces 62 of the elliptical tissue-receiving region 46. Since the tissue will be partially closed together at this portion of the elliptical (compared to a circular opening), it will be easier for the needles to find target tissue and become firmly anchored. Preferably, the total peripheral distance over the needle guide 14 will not vary, with only the shape changing. By providing such a constant peripheral distance, hemostasis is maintained as the device is advanced and the tendency to tear or otherwise damage the tissue surrounding the puncture will be reduced.

Figure 6:
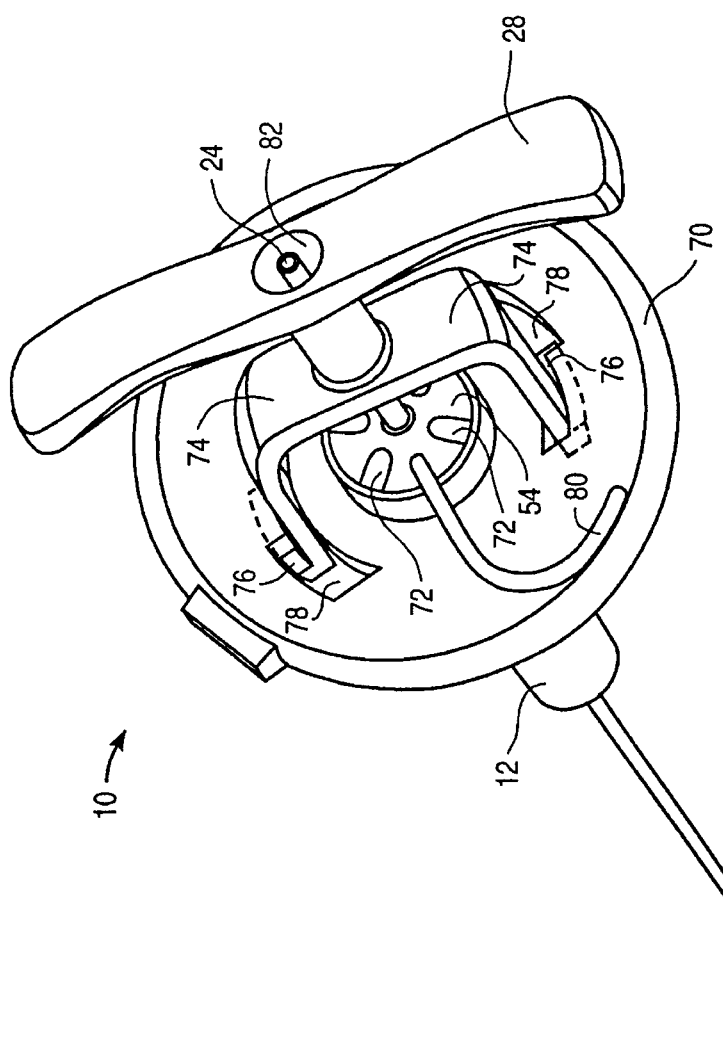
FIG. 6 is a perspective view of the proximal end of the suturing device of FIG. 1.

Referring now to FIGS. 1 and 6, a proximal finger grip 70 is attached to the proximal end of guide body 12. The proximal end of the guide body 12 includes needle lumens 72 which permit exit of the needles 20 after they are fully withdrawn through the guide body. Handle 28 includes a U-shaped locking member 74 having a pair of keys 76. The keys 76 are received in slots 78 formed in the finger grip 70. Rotation of the handle 28 in a clockwise direction, as viewed in FIG. 6, will lock the keys 76 within the slots 78. Conversely, rotation of the handle 28 in a counter-clockwise direction releases the handle. In this way, the handle 28, shaft 24, and needles 20 may be locked to prevent accidental needle deployment as the suturing device 10 is introduced through a tissue tract, as described in more detail hereinafter.

A blood marker tube 80 is attached to a lumen in the guide body, which in turn is attached to the blood marker port 58. When the suturing device is introduced into a blood vessel so that the marker port 58 lies within the blood vessel lumen (and is thus exposed to blood pressure), blood will appear at the open end of tube 80, indicating proper positioning of the device. Shaft 24 terminates in an aperture 82 in handle 28. The proximal end of shaft 24 thus serves as an exit port for a guide wire when the device is introduced over a guide wire.

Figure 7:
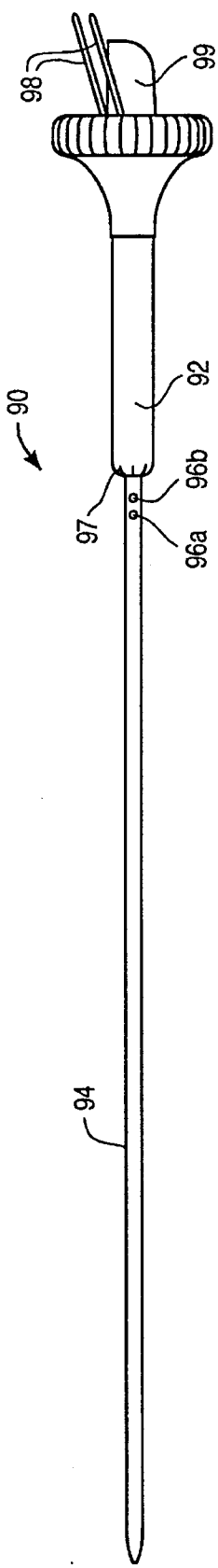
FIG. 7 is a side view of a predilator device constructed in accordance with the principles of the present invention.
Figure 8:
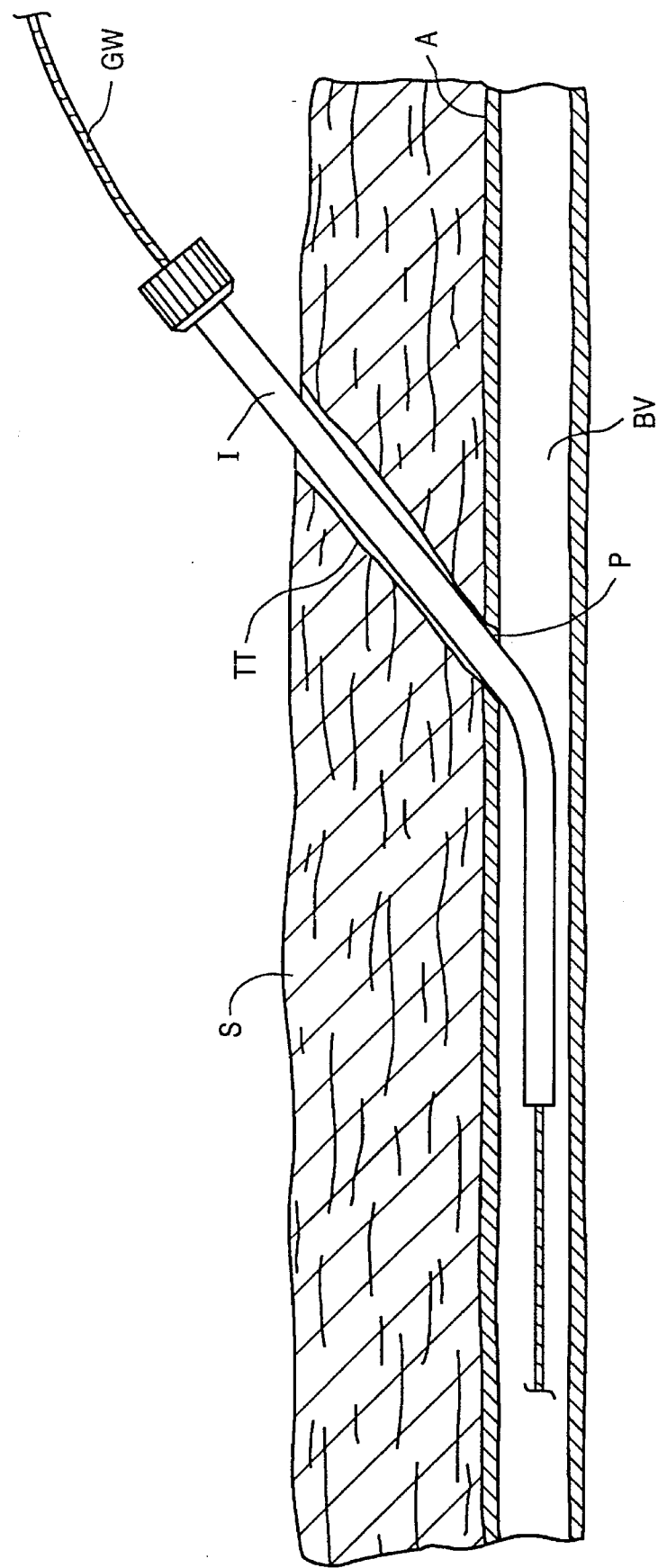
FIGS. 8–14 illustrate use of the suturing device of FIG. 1 and predilator device of FIG. 7 in performing a vascular suturing procedure according to the method of the present invention.

Referring now to FIG. 7, a predilator 90 comprises a cylindrical body 92 having dimensions generally equal to, or preferably slightly greater than (by 1 mm to 2 mm in diameter), those described above for the guide body 12 of the suturing device 10. The predilator 90 further comprises a flexible shaft 94, which is preferably tubular and includes a lumen for receiving a guide wire to permit vascular introduction. The diameter of shaft 94 is generally equal to that described above for the flexible needle sheath 16 of the suturing device 10, but will typically be shorter. The dilator 90 further includes at least one and preferably a pair of blood marker ports 96 which are disposed on the shaft 94 close to the distal end of predilator body 92. The ports will preferably be located within a distance in the range from 2 mm to 15 mm of the distal end, with a proximal port 96b located within a distance in the range from 2 mm to 10 mm and a distal port 96a located within a distance in the range from 5 mm to 15 mm. The blood detection ports 96 connected to tubes 98 which permit the detection of blood when the predilator has been properly positioned, as described in more detail hereinbelow. A finger grip 99 extends proximally from the cylindrical body 92 and is connected to the shaft 94. The shaft and grip 99 are rotationally mounted within the body 92 so that the user can grasp the body in one hand, the grip in the other hand, and manually rotate the shaft relative to the body. Serrations 97 at the distal end of body 92 help dilate the tissue tract as the body is rotated and advanced toward the blood vessel.

The primary function of the predilator 90 is to dilate the subcutaneous tissue between the skin and the artery prior to introduction of the suturing device 10. Successful deployment of the predilator 90 facilitates subsequent introduction of the suturing device 10 and is an indication that the device 10 can be successfully deployed. Blood detection ports 98 are spaced-apart to provide visual indication to the user of the position of the predilator 90 relative to the blood vessel. The distal port 96a first enters the blood vessel and blood will appear in one of the tubes 98 prior to final positioning of the predilator 90. The distal end of the body 92 may then be carefully positioned over the adventitial surface of the blood vessel until the proximal port 96b enters the blood vessel and blood appears in the second tube 98. Rotation of the body 92 relative to the shaft 94 during the deployment helps dilate the tissue tract without risk of injury to the blood vessel from rotation of the shaft. Presence of the shaft 94 in the puncture helps maintain hemostasis during the predilation procedure.

Exemplary dimensions for the predilator 90 are body 92 length in the range from 30 mm to 100 mm, a body diameter in the range from 5 mm to 15 mm, the flexible shaft has a length in the range from 100 mm to 400 mm and a diameter in the range from 2 mm to 7 mm.

Referring now to FIGS. 8–14, use of the suturing device 10 and predilator 90 for closing a vascular puncture P will be described. The vascular puncture P is formed in the wall of blood vessel BV which is located at the distal end of a tissue tract TT by the Seldinger technique. An introducer sheath I is placed over a guide wire GW passing percutaneously beneath the patient's skin S. The situation illustrated in FIG. 8 will be typical of the end of a wide variety of interventional and/or diagnostic procedures, including angiography, ultrasonic imaging, angioplasty, atherectomy, intravascular drug delivery, and the like. It is desirable that the introducer sheath I be removed and that the vascular puncture be closed and sealed.

Figure 9:
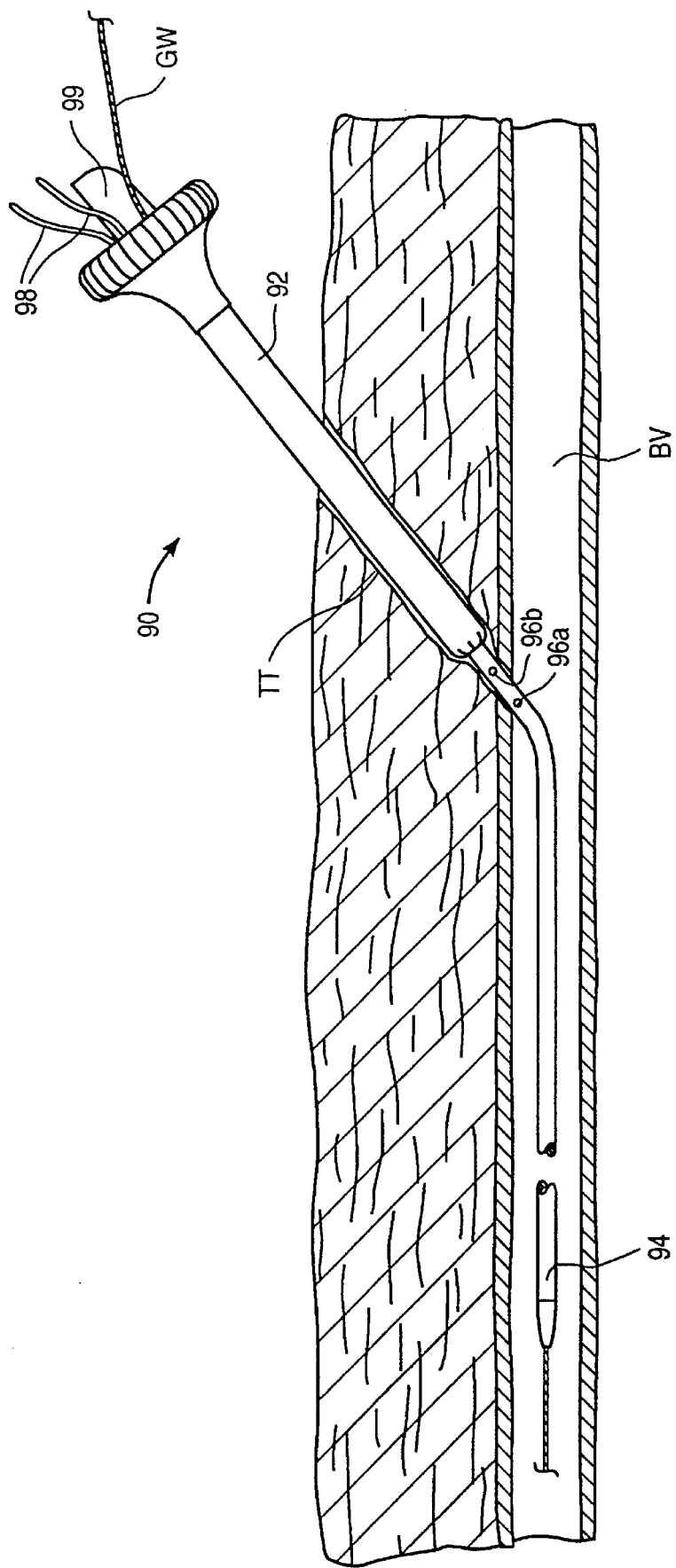

Referring now to FIG. 9, the method of the present invention begins by introducing the predilator 90 inward through the tissue tract TT over the guide wire GW. The predilator 90 is introduced until the flexible shaft 94 has fully entered into the lumen of blood vessel BV so that at least one of the blood marker ports 96 is exposed to blood flow. Thus, blood can be observed at least one of the tubes 98, indicating that the predilator 90 has been properly positioned. The ability to properly position the predilator is predictive of the ability to subsequently introduce the suturing device 10.

Figure 10:
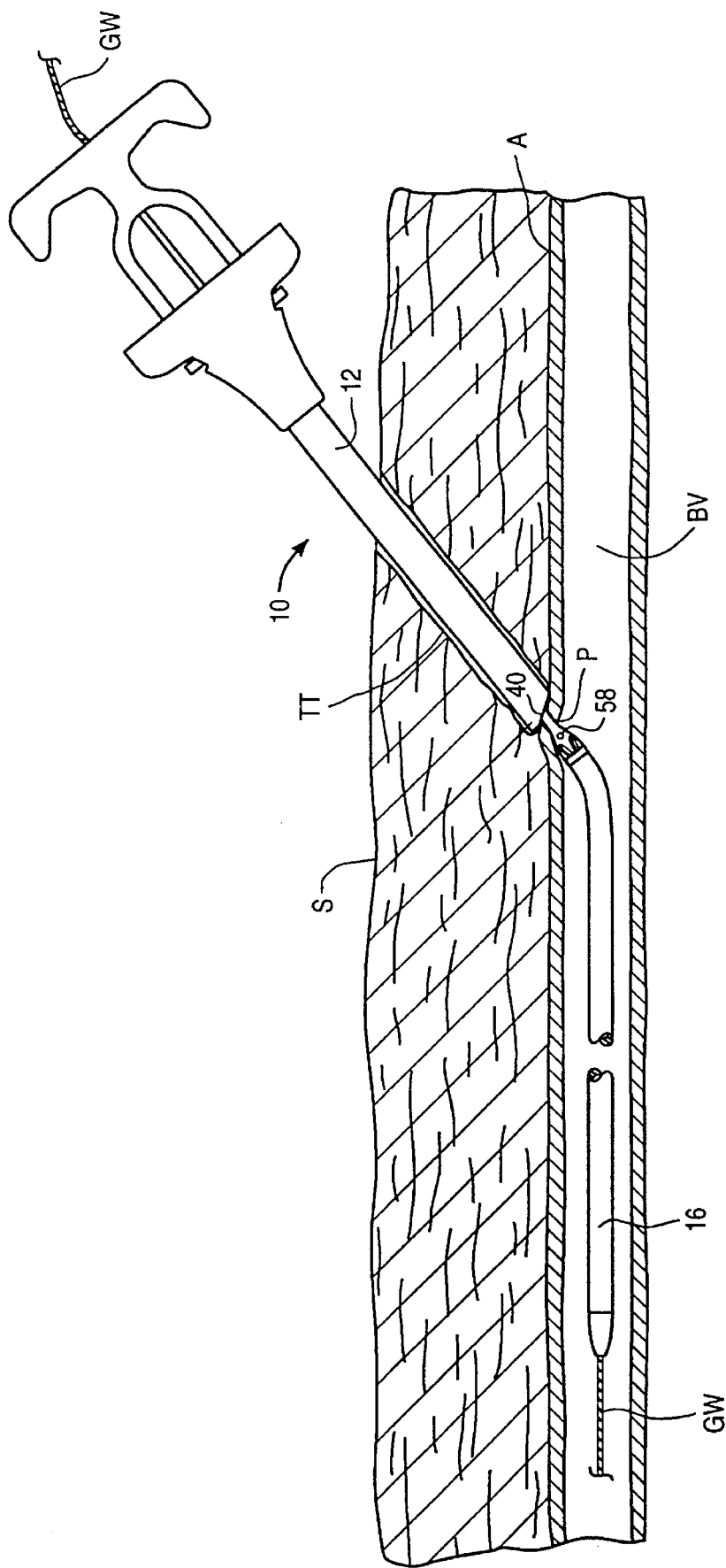

Referring now to FIG. 10, the predilator 90 is removed and replaced with the suturing device 10 which is also introduced over the guide wire GW. Device 10 is introduced so that the blood marker port 58 just enters the blood vessel BV lumen, as illustrated. At that point, the contact surface at distal end 40 of the guide body 12 will lie generally flat over the adventitial surface of the blood vessel wall in the region surrounding the puncture P. The flexible needle sheath 16 will be fully inserted into the blood vessel BV lumen with the needles remaining undeployed within the sheath.

Figure 11:
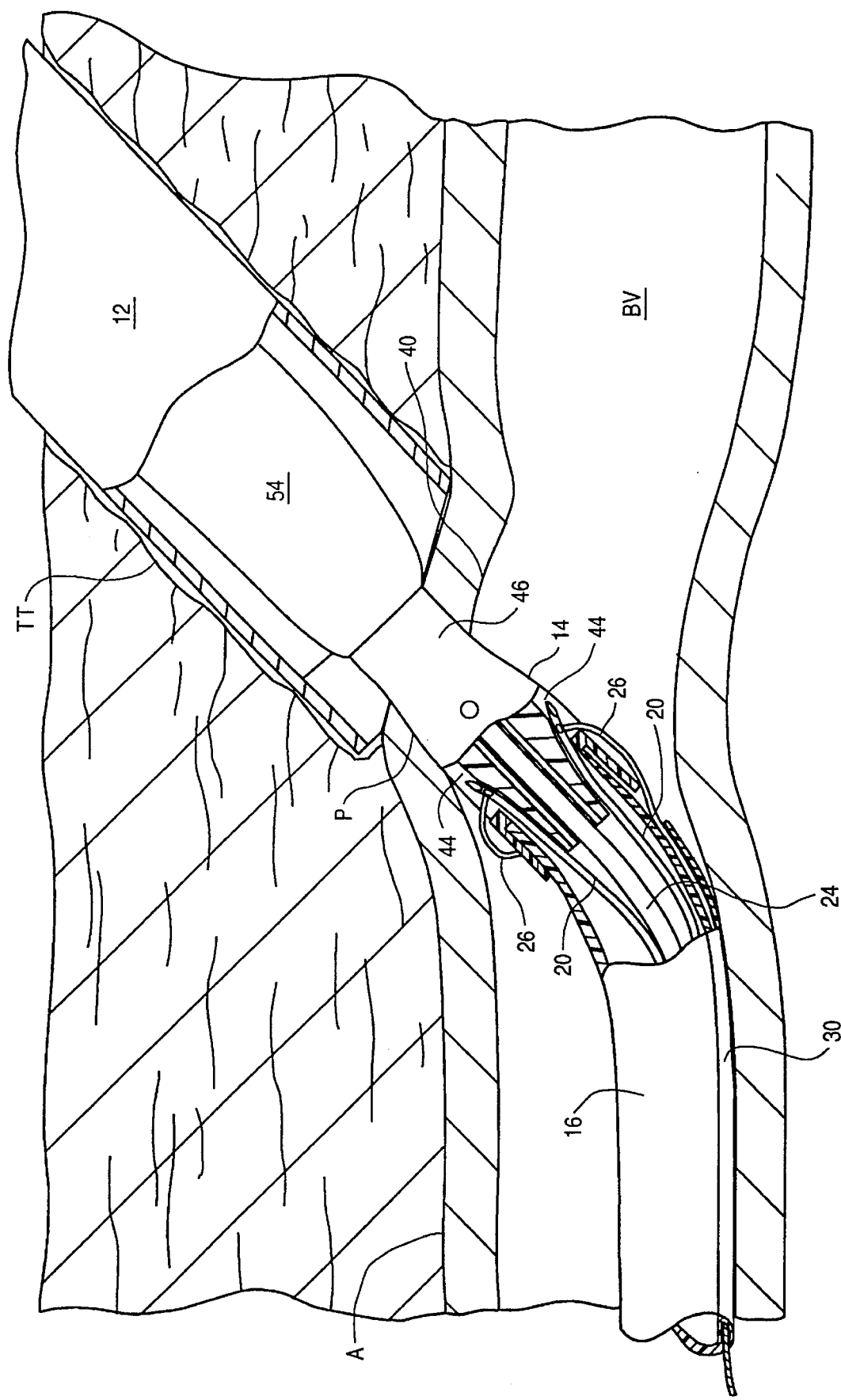
Figure 12:
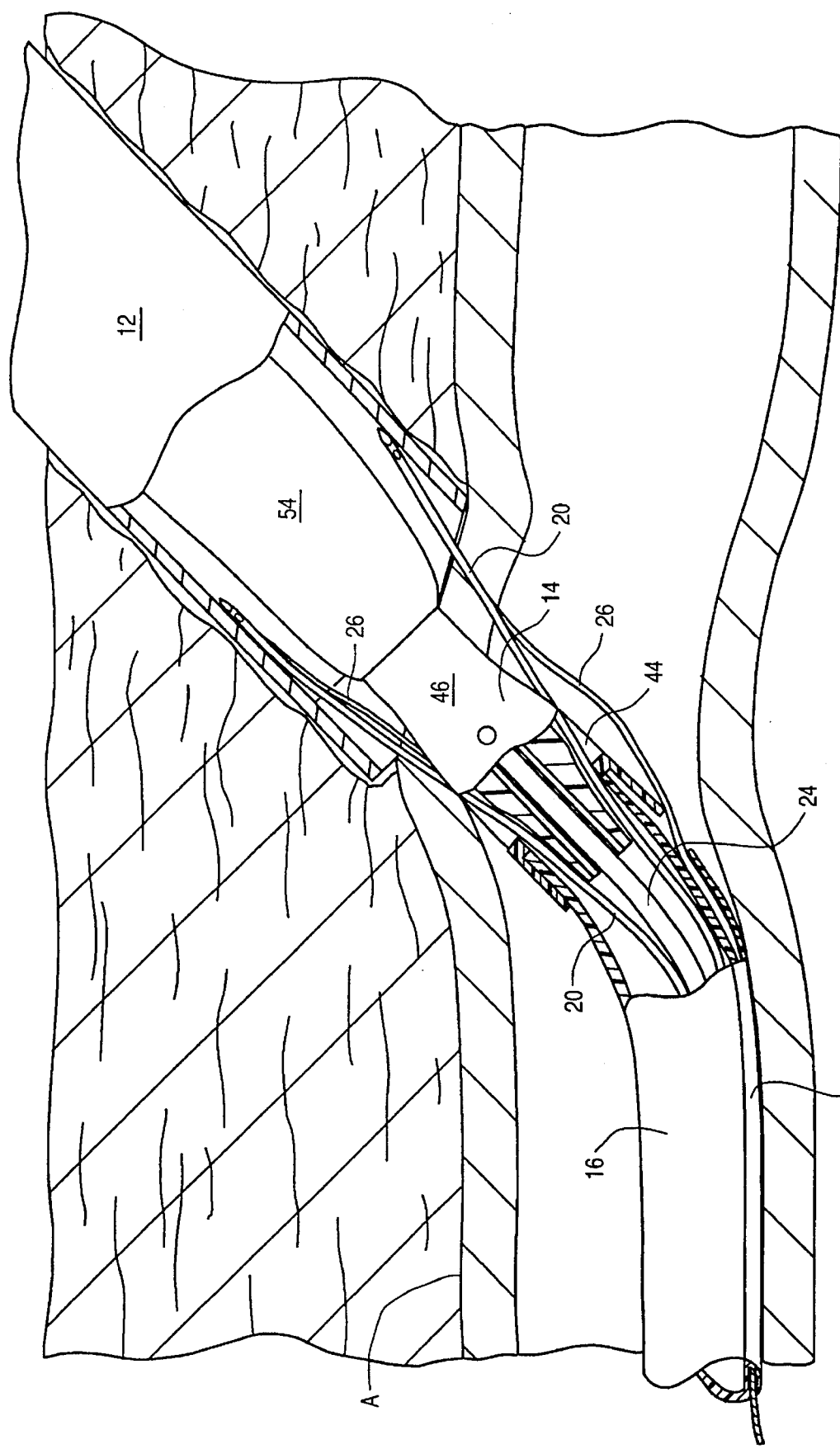

Referring now to FIG. 11, the position of the needle guide 14 within puncture P will be described in more detail. The wall of blood vessel BV is received over the tissue-receiving region 46 of the needle guide 14. The needles 20, remain retracted within guide channels 44, with suture 26 remaining within side lumen 30. For convenient illustration, only two needles and a single length of suture 26 are illustrated in FIGS. 11 and 12. The preferred embodiment, of course, will include four needles with two lengths of suture therebetween.

Figure 13:
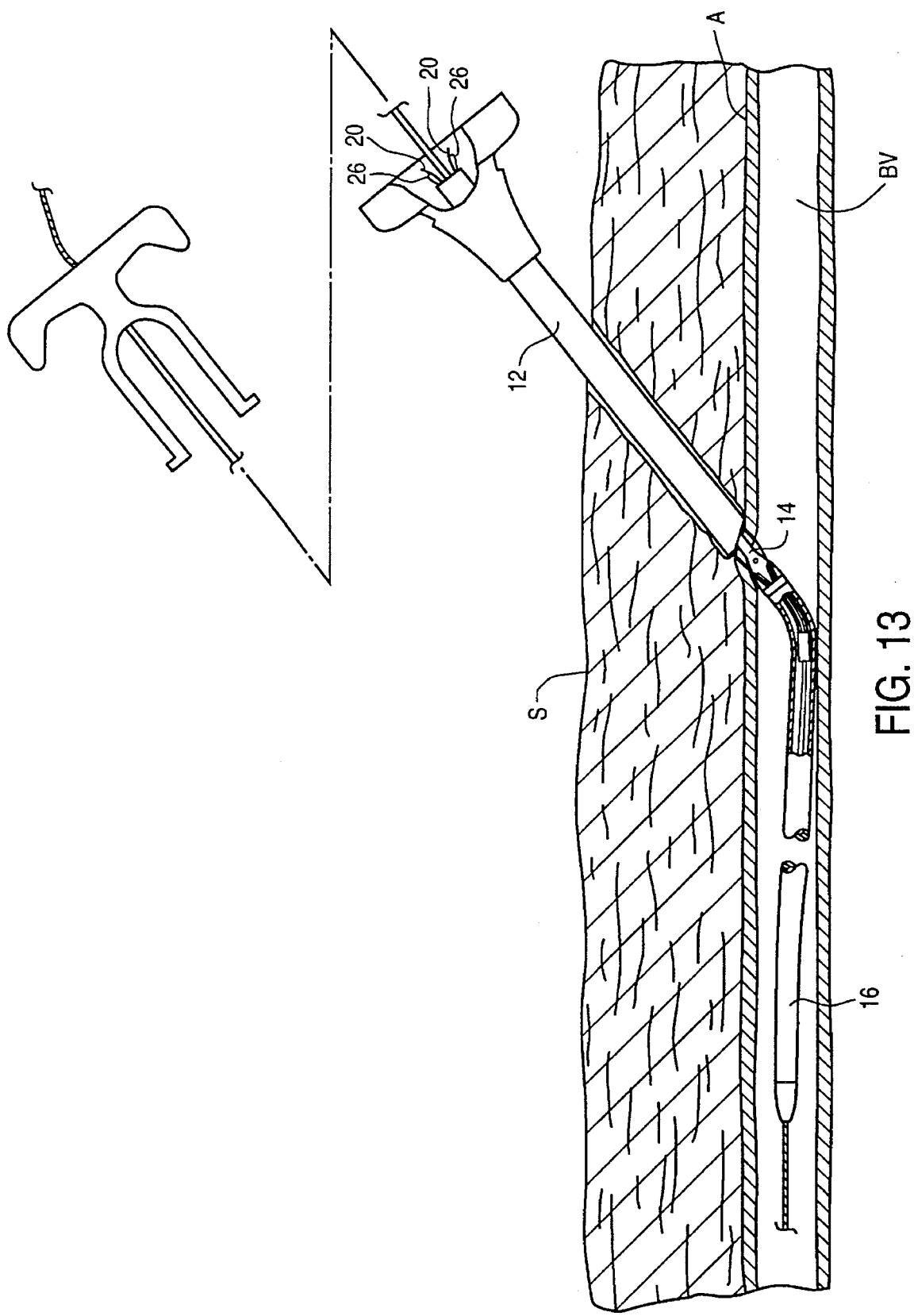

The contact surface at distal end 40 of the guide body 12 lies generally flat over the adventitial wall A of the blood vessel BV, providing a particularly good target for the needles 20 as they are advanced. As best seen in FIG. 12, the needles 20 will exit from the guide channels 44, through the blood vessel wall and into needle lumens within the guide body 12. The needles 20 may then be drawn proximally fully through the guide body 12, as illustrated in FIG. 13. The needles emerge from the proximal end of the guide body, with the suture 26 attached thereto. The needles 20 may then be pulled from the holster 22 in order to gain access to the free ends of the suture. Alternatively, the suture may be removed from the proximal ends of the needles 20, and the needles then reciprocated distally back into the sheath 16 in order to permit withdrawal of the suturing device. It should be noted that, for safety purposes, the needles can always be retracted distally back into the sheath 16 in order to terminate a procedure and remove the suturing device 10.

Figure 14:
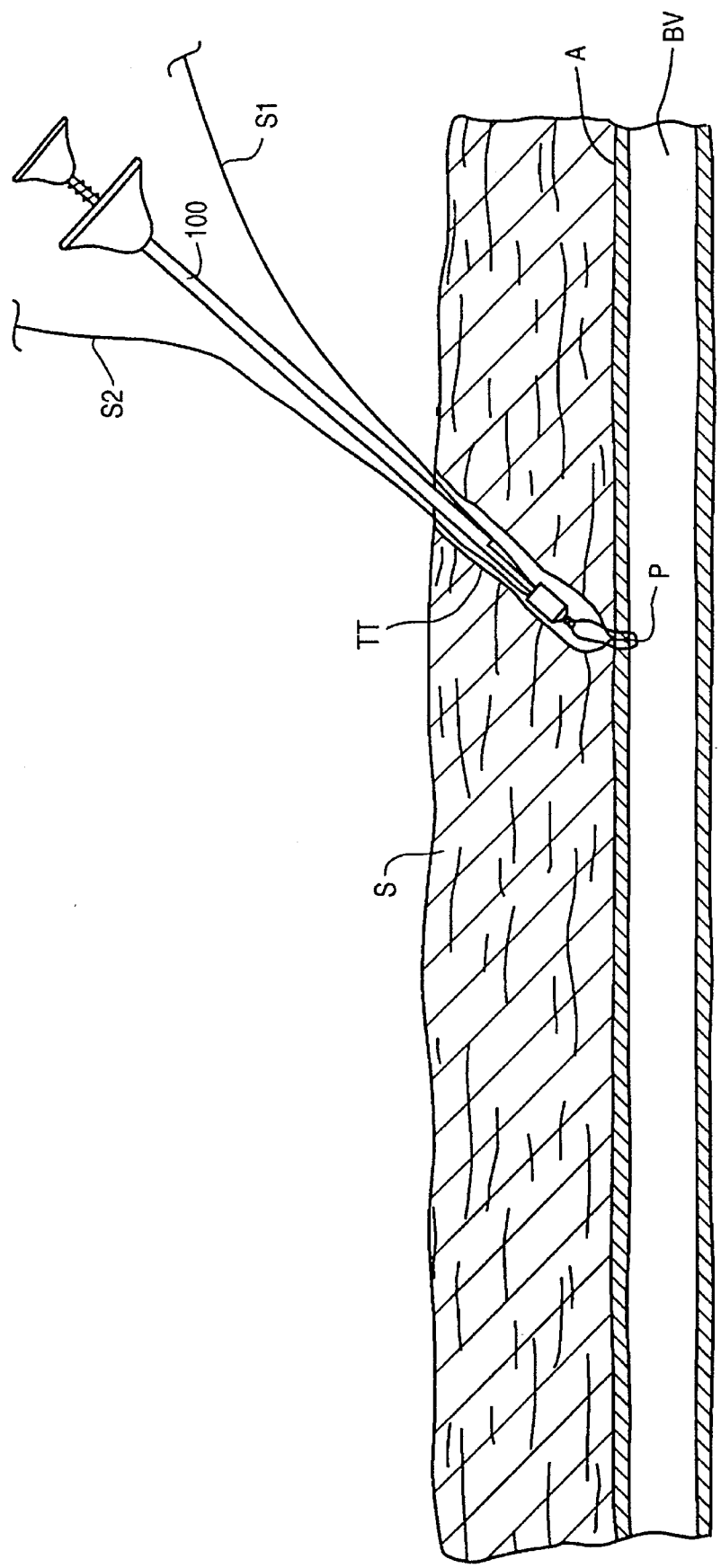

After the free ends of the suture and/or the needles 20 are removed or retracted, the suturing device 10 can be withdrawn together with the guide wire GW. The vascular punctures P can then be closed and sealed by tying free ends of the suture S1 and S2, as illustrated in FIG. 14. Typically, the suture will be tied outside of the tissue tract TT and then the knot advanced through the tissue tract to the adventitial surface A using a knot pusher 100, such as that illustrated in co-pending application Ser. No. 08/522,211 which is a continuation of application Ser. No. 08/252,310 (Attorney Docket No. 15508-14),the full disclosure of which is incorporated herein by reference. The suture can also be fastened using a wide variety of fasteners or other mechanical closure elements.

Although the foregoing invention has been described in some detail by way of illustration and example, for purposes of clarity of understanding, it will be obvious that certain changes and modifications may be practiced within the scope of the appended claims.

What is claimed is:

1. A suturing device comprising:

a guide body having a proximal end, a distal end, a central axis, and a contact surface at the distal end oriented at an angle in the range from 30° to 80° relative to the central axis;

a needle guide connected to and spaced-apart from the distal end of the guide body, wherein said needle guide and guide body together define a tissue-receiving region therebetween and wherein at least one needle channel on said needle guide or said guide body is oriented to direct a needle passing therethrough into the tissue-receiving region;

a shaft reciprocatably mounted within the guide body and the needle guide; and at least one needle carried by the shaft and disposed within the guide channel so that a sharpened proximal tip of the needle can be drawn from the needle guide, through the tissue-receiving region and into the guide body.

2. A suturing device as in claim 1, wherein the contact surface includes an annular ring.

3. A suturing device as in claim 2, wherein the guide body includes a tubular shell having a distal end which defines the annular ring.

4. A suturing device as in claim 1, wherein the guide body is cylindrical and the contact surface is defined by a generally planar section through the distal end.

5. A suturing device as in claim 1, wherein the contact surface spans an area in the range from 40 mm$^2$ to 100 mm$^2$.

6. A suturing device as in claim 1, wherein the guide body has at least one lumen for receiving said at least one needle after said needle has been drawn through the tissue-receiving region.

7. A suturing device as in claim 1, wherein the proximal end of the needle guide has a non-circular periphery which disposes surrounding tissue to receive a needle from the needle guide channel.

8. A suturing device as in claim 7, wherein the asymmetric periphery of the proximal end of the needle guide is generally elliptical.

9. A suturing device as in claim 8, wherein the distal end of the needle guide has a generally circular periphery, wherein the guide channel is oriented to pass the needle by a major surface of the elliptical proximal end.

10. A suturing device as in claim 8, wherein the needle guide has a substantial constant peripheral dimension over its length from the guide channels to the elliptical section which receives the tissue.

11. A suturing device as in claim 1, further comprising means for releasably securing the shaft to the guide body to prevent relative axial movement.

12. A suturing device as in claim 11, wherein the means for releasably securing comprises at least one slot formed at the proximal end of the guide body and at least one key disposed at the proximal end of the shaft, whereby the key can be engaged and disengaged in the slot by rotation of the shaft relative to the guide body.

13. An improved suturing device of the type including a guide body having a proximal end and distal end and means on the guide body for translating at least one needle relative to the guide body, said needle having a sharpened distal tip disposed in the proximal direction, wherein the improvement comprises a generally planar contact surface disposed at a distal end of the guide body and oriented at an angle in the range from 30° to 80° relative to a central axis of the guide body, wherein the translating means translates the needle from a first position with the sharpened distal tip spaced distally from the planar surface to a second position with the sharpened distal tip within the guide body.

14. An improved suturing device as in claim 13, wherein the contact surface includes an annular ring.

15. An improved suturing device as in claim 14, wherein the guide body includes a tubular shell having a distal end which defines the annular ring.

16. An improved suturing device as in claim 13, wherein the guide body is cylindrical and the contact surface is defined by a generally planar section through the distal end.

17. An improved suturing device as in claim 13, wherein the contact surface spans an area in the range from 40 mm$^2$ to 100 mm$^2$.

18. A suturing device comprising:

a guide body having a proximal end and a distal end;

a needle guide having a proximal end fixedly attached to the distal end of the guide body and a distal end having at least two needle guide channels, wherein said proximal end is disposed between the distal end of the guide body and the needle guide channels and has a non-circular periphery which is spaced inwardly from the two needle guide channels to position surrounding tissue to receive needles from the needle guide channels;

a pair of needles having a length of suture extending therebetween; and a shaft reciprocatably mounted within the guide body and carrying the needles to reciprocate said needles within the needle guide channels.

19. A suturing device as in claim 18, wherein the non-circular periphery of the proximal end of the needle guide is generally elliptical.

20. A suturing device as in claim 19, wherein the distal end of the needle guide has a generally circular periphery wherein the guide channels are oriented to pass needles by a major surface of the elliptical proximal end.

21. A suturing device as in claim 19, wherein the needle guide has a substantial constant peripheral dimension over its length from the guide channels to the elliptical section.

22. A suturing device as in claim 18, wherein the guide body has a contact surface at its distal end oriented at an angle in the range from 30° to 80° relative to a central axis of the guide body.

23. A suturing device as in claim 22, wherein the contact surface includes an annular ring.

24. A suturing device as in claim 23, wherein the guide body includes a tubular shell having a distal end which defines the annular ring.

25. A suturing device as in claim 22, wherein the guide body is cylindrical and the contact surface is defined by a generally planar section through the distal end.

26. A suturing device as in claim 22, wherein the contact surface spans an area in the range from 40 mm$^2$ to 100 mm$^2$.

27. A suturing device as in claim 18, wherein the guide body has at least two lumens for receiving the pair of needles after said needles have been reciprocated proximally by the shaft.

28. A suturing device as in claim 18, further comprising means for releasably securing the shaft to the guide body to prevent relative axial movement.

29. A suturing device as in claim 28, wherein the means for releasably securing comprises at least one slot formed at the proximal end of the guide body and at least one key disposed at the proximal end of the shaft, whereby the key can be engaged and disengaged in the slot by rotation of the shaft relative to the guide body.

30. A suturing device comprising:

a guide body having a proximal end and a distal end, wherein the guide body has at least two lumens for receiving the pair of needles after said needles have been reciprocated proximally by a shaft;

a needle guide having a proximal end attached to the distal end of the guide body and a distal end having at least two needle guide channels;

a pair of needles having a length of suture extending therebetween;

wherein shaft is reciprocatably mounted within the guide body and carries the needles to reciprocate said needles within the needle guide channels; and means for releasably securing the shaft to the guide body to prevent relative reciprocation.

31. A suturing device as in claim 30, wherein the means for releasably securing comprises at least one slot formed at the proximal end of the guide body and at least one key disposed at the proximal end of the shaft, whereby the key can be engaged and disengaged in the slot by rotation of the shaft relative to the guide body.

32. A suturing device as in claim 30, wherein the guide body has a contact surface at its distal end oriented at an angle in the range from 30° to 60° relative to a central axis of the guide body.

33. A suturing device as in claim 32, wherein the contact surface includes an annular ring.

34. A suturing device as in claim 33, wherein the guide body includes a tubular shell having a distal end which defines the annular ring.

35. A suturing device as in claim 32, wherein the guide body is cylindrical and the contact surface is defined by a generally planar section through the distal end.

36. A suturing device as in claim 32, wherein the contact surface spans an area in the range from 40 mm² to 100 mm².

37. A suturing device as in claim 32, wherein the proximal end of the needle guide has a non-circular asymmetric periphery which disposes surrounding tissue to receive a needle from the needle guide channel.

38. A suturing device as in claim 37, wherein the asymmetric periphery of the proximal end of the needle guide is generally elliptical.

39. A suturing device as in claim 38, wherein the distal end of the needle guide has a generally circular periphery, wherein the guide channels are oriented to pass needles by the major surface of the elliptical proximal end.

40. A suturing device as in claim 38, wherein the needle guide has a substantially constant peripheral dimension over its length from the guide channels to the elliptical section which receives the tissue.

41. A predilator comprising:

a body having a proximal end and a distal end; and a flexible tube having a proximal end attached to the distal end of the body;

wherein a guide wire lumen extends continuously from the distal end of the flexible tube to the proximal end of the body and wherein at least one blood marker lumen extends from a marker port disposed near the proximal end of the flexible tube to the proximal end of the body and wherein the flexible tube is rotatably attached to the body.

42. A predilator as in claim 41, wherein the body is a rigid cylinder having a length in the range from 30 mm to 100 mm and a diameter in the range from 5 mm to 15 mm, and wherein the flexible tube has a length in the range from 100 mm to 400 mm and a diameter in the range from 2 mm to 7 mm.

43. A predilator as in claim 42, wherein the marker port is located at a distance from the distal end of the body in the range from 2 mm to 15 mm.

44. A predilator as in claim 41, having a first marker lumen with a proximal marker port located at a distance from the distal end of the body in the range from 2 mm to 10 mm and a second marker lumen with a distal marker port located at a distance from the distal end of the body in the range from 5 mm to 15 mm.

45. A system for suturing a vascular puncture at the distal end of a tissue tract, said system comprising:

a predilator including a body having a proximal end and a distal end, and a flexible tube having a proximal end attached to the distal end of the body and a distal end, wherein continuous guide wire lumen extends from the distal end of the flexible tube to the proximal end of the body; and a suturing device including (a) a guide body having a proximal end and a distal end, wherein an axial passage is disposed within the guide body to receive the needle from the tissue-receiving region at the distal end and guide the needle to the proximal end, (b) a sheath extending distally from the guide body, and (c) a needle slidably disposed within the sheath so that the needle can be drawn proximally from the sheath into the guide body, wherein the diameter of the guide body is substantially the same as that of the predilator body.

46. A system as in claim 45, wherein the predilator body is a rigid cylinder having a length in the range from 30 mm to 100 mm, and wherein the flexible tube has a length in the range from 100 mm to 400 mm and a diameter in the range from 2 mm to 7 mm.

47. A system as in claim 46, wherein the marker port is located at a distance from the distal end of the body in the range from 2 mm to 15 mm.

48. A system as in claim 47, wherein the predilator has a first marker lumen with a proximal marker port located at a distance from the distal end of the body in the range from 2 mm to 10 mm and a second marker lumen with a distal marker port located at a distance from the distal end of the body in the range from 5 mm to 15 mm.

49. A system as in claim 46, wherein the flexible tube of the predilator is rotatably attached to the body.

50. A system as in claim 45, wherein the needle is longer than the guide body so that the needle can be advanced through the guide body by pushing on its trailing end.

51. A system as in claim 45, further comprising a needle guide having a needle guide channel disposed adjacent the sheath.

52. A system as in claim 51, wherein the needle guide has a pair of needle guide channels disposed on opposite sides of the needle guide.

53. A system as in claim 52, comprising a pair of needles having suture attached, with one needle slidably mounted in each of the guide channels.

54. A system as in claim 53, wherein the pair of needles has a continuous length of suture attached therebetween.

55. A system as in claim 54, wherein the needle guide is attached to the guide body on a distal side of the tissue-receiving region.

56. A system as in claim 55, further comprising a shaft having a proximal end and a distal end, wherein the shaft is slidably mounted within the sheath and the needles are carried on the distal end of the shaft.

57. A system as in claim 45, wherein the predilator body has a diameter which is larger by 1 mm to 2 mm than that of the guide body and the flexible tube has a diameter which is substantially equal to that of the flexible sheath.

58. A method for suturing a puncture site in a blood vessel wall disposed at the distal end of a percutaneous tissue tract, said method comprising:

introducing a predilator having a body and a distally extending flexible tube to the puncture site so that said body lies within the tissue tract and the flexible tube lies in a lumen of the blood vessel;

confirming that the predilator is properly positioned relative to the puncture site;

removing the predilator;

introducing a suturing device having a guide body and a distally extending flexible sheath to the puncture site so that said guide body lies within the tissue tract and the flexible sheath lies within the blood vessel lumen;

drawing a needle carrying a length of suture from the sheath through the blood vessel wall adjacent the punctures and outward through the tissue tract; and securing a loop in the suture to close the punctures.

59. A method as in claim 58, wherein the predilator body has a diameter which is larger by 1 mm to 2 mm than that of the guide body, whereby successful introduction of the predilator is predictive of successful introduction of the suturing device.

60. A method as in claim 58, wherein proper positioning of the predilator is confirmed by observing blood within a marker lumen having a port on the flexible tube immediately distal to the distal end of the guide body.

61. A method as in claim 60, further comprising positioning the suturing device by observing blood within a marker lumen in the guide body having a port between the flexible sheath and the distal end of the guide body.

62. A method as in claim 58, wherein a pair of needles having a length of suture therebetween are simultaneously drawn through the blood vessel wall to form a loop having free ends extending out through the tissue tract.

* * * * *